United States Patent [19]
Taylor et al.

[11] Patent Number: 5,090,903
[45] Date of Patent: Feb. 25, 1992

[54] DENTAL PROSTHESIS WITH CONTROLLED FLUID DISPENSING MEANS

[76] Inventors: Roy M. Taylor, 2345 Cobb Pkwy., Smyrna, Ga. 30080; Leonard Ross, 2985 Valley Ridge Dr., Decatur, Ga. 30032

[21] Appl. No.: 642,787

[22] Filed: Jan. 18, 1991

[51] Int. Cl.⁵ .............................................. A61G 17/02
[52] U.S. Cl. ....................................... 433/80; 433/229
[58] Field of Search ......................... 433/80, 215, 229; 604/77, 80, 890.1

[56] References Cited
U.S. PATENT DOCUMENTS

| | | | |
|---|---|---|---|
| H150 | 11/1986 | Hankner et al. | 604/890.1 X |
| 589,712 | 9/1897 | Fouquier | 604/77 X |
| 1,978,217 | 10/1934 | Muckerjee | 604/77 |
| 3,481,329 | 12/1969 | Warren, Jr. | 604/77 X |
| 4,020,558 | 5/1977 | Cournut et al. | 433/80 |
| 4,431,428 | 2/1984 | Schmer | 604/890.1 |
| 4,455,143 | 6/1984 | Theeuwes et al. | 604/890.1 |
| 4,676,752 | 6/1987 | Lefkowitz | 433/229 |
| 4,741,700 | 5/1988 | Barabe | 433/229 |
| 4,959,051 | 9/1990 | Glass et al. | 604/77 |
| 4,959,052 | 9/1990 | Cox | 604/77 |

FOREIGN PATENT DOCUMENTS 8600519 1/1986 World Int. Prop. O. ........ 604/890.1

Primary Examiner—Robert P. Swiatek
Assistant Examiner—Nicholas D. Lucchesi
Attorney, Agent, or Firm—Hopkins, Thomas, Kerr

[57] ABSTRACT

A system for automatically and progressively dispensing fluids into an individual's mouth comprises a dental prostheses such as a bridge having an interior cavity with a plurality of chambers defined therein. A first passageway communicates between the inner chamber and the interior of the mouth for progressive delivery of fluid from the chamber into the mouth. A second passageway communicates between the outer chamber and the outer surface of the bridge and functions as a vent. Spaced parallel walls within the cavity define the chambers therein and openings in the walls communicate between adjacent chambers. The walls, openings, and passageways are positioned and oriented such that fluid is dispensed into the mouth progressively from the inner chamber during waking hours when the wearer is in a standing or upright position and is not dispensed during the night time or sleeping hours when the wearer is in an inclined or lying position. The wall holes are positioned such that the inner chamber of the cavity is refilled during sleeping hours for subsequent dispensing when the wearer wakes and arises.

12 Claims, 3 Drawing Sheets

DENTAL PROSTHESIS WITH CONTROLLED FLUID DISPENSING MEANS

TECHNICAL FIELD

This invention relates to dispensers and more particularly dental prostheses adapted to dispense fluids such as medications and breath fresheners automatically into the mouth.

BACKGROUND OF THE INVENTION

Many kinds of beneficial substances such as medications and breath fresheners have long been administered orally in liquid form because of the ease and convenience of such oral administration. In many cases, and particularly in the case of some medications, it is highly desirable and can even be critical that the substance be administered in a controlled progressive manner throughout the day. In some instances, it is important that the substance be administered throughout the daytime or waking hours, but not during periods of sleep. This can be the case with some medications and is particularly true for administration of breath fresheners, for which dispensing during the night or while sleeping serves no purpose and is wasteful.

In the past, carefully controlled oral administration of medications, breath fresheners, and other substances has presented problems because individuals often forget or neglect administration, forget to keep the substances with them when traveling, or generally fail to apply carefully the proper dosages at the proper times. Accordingly, a number of devices have been proposed for administering such substances automatically without dependence upon an individual's memory or care.

U.S. Pat. No. 3,153,855 of Holland, for example, discloses a denture having a tooth with a reservoir that receives and contains a fluid such as breath freshener. A manually operable ball and socket valve is adapted to be brushed periodically with the tongue to release a small amount of the fluid from the reservoir into the mouth. While such a device represents some improvement over manual administration, it nevertheless fails to address the above discussed problems fully because the timing and dosage of each administration still relies upon individual memory and discretion. Furthermore, no means are provided to insure that fluid is not dispensed and wasted during sleep should the sleeper's tongue inadvertently brush the valve.

Other examples of attempts to provide automatic and controlled dispensing of liquids into the mouth are disclosed in U.S. Pat. Numbers 3,503,127 of Kasdin and 4,106,501 of Ozbev. The devices of these patents, like that of Holland, while representing improvements over manual methods, nevertheless fall short of a complete and reliable solution to the problems discussed hereinabove and generally embody particular problems and shortcomings inherent in their respective designs.

It is therefore clear that a continuing and heretofore only partially and unsuccessfully addressed need exists for a reliable and economical method and enabling apparatus adapted to dispense liquids such as medications and breath fresheners into the mouth automatically in a controlled progressive manner and independently of individual care and discretion. Such a method and apparatus should also be configured for automatic discontinuation of the liquid dispensing process during times of sleep or rest to prevent waste. It is to the provision of such a method and apparatus that the present invention is primarily directed.

SUMMARY OF THE INVENTION

The present invention, in one preferred embodiment thereof, comprises a dental prothesis in the form of a bridge having a central artificial tooth formed with and wedged between front and rear artificial teeth. Such bridges are generally secured in the mouth with the front and rear artificial teeth mounted and secured on spaced stubs that have been prepared by grinding down one of the patient's natural teeth on each side of a gap to be spanned by the central artificial tooth of the bridge.

The central artificial tooth is formed with a generally spherical interior cavity having a pair of spaced divider walls that separate the cavity into an inner chamber normally positioned adjacent the interior of the mouth, and outer chamber normally positioned adjacent the cheek, and a central chamber disposed between the inner and outer chambers. The walls of the cavity are oriented to slope upwardly from the cheek side of the bridge toward the roof of a patient's mouth when the wearer of the bridge is standing or sitting in an upright orientation.

Each wall is formed with a small opening at its upper peripheral edge that communicates between adjacent chambers of the cavity. A first passageway communicates between the inner chamber of the cavity and the inside surface of the bridge central tooth for delivering liquid from the inner chamber to the mouth and a second passageway communicates between the outer chamber and the cheek side surface of the bridge central tooth to function as a vent through which air can enter the cavity to displace dispensed fluid.

In use, the chambers of the cavity are filled with a fluid such as medication or breath freshener that is to be dispensed into the mouth. With the bridge wearer standing or sitting in an upright position, liquid from within the inner chamber of the cavity flows through the first passageway and is dispensed into the mouth. The size of the passageway in conjunction with the viscosity of the fluid determines the rate at which fluid is dispensed and the size of the cavity's inner chamber determines total volume of liquid dispensed. The liquid thus continues to be dispensed into the mouth at a slow progressive rate as long as the wearer is standing or until the dosage within the inner chamber of the cavity is drained.

When the patient lies down in a reclined position for sleep or rest, the orientation of the walls within the cavity and the placement of the passageways insures that delivery of liquid to the mouth is discontinued. Furthermore, during such periods of sleep, the inner chamber of the cavity is automatically refilled as liquid passes from the central and outer chambers through the peripheral wall openings and into the inner chamber. Upon awakening and rising to an upright position, the inner chamber is again filled and liquid is dispensed into the mouth as summarized above.

Thus, it is now seen that a unique method and apparatus is provided that dispenses liquids such as medications and breath fresheners into the mouth automatically and in a controlled progressive manner. Dispensing is automatically discontinued to prevent unwanted waste and the delivery chamber is automatically refilled during times when a wearer is lying down in a reclined orientation for sleep or rest. The apparatus can be configured to dispense only a measured dosage of fluid

DETAILED DESCRIPTION OF THE PREFERRED EMBODIMENT

Figure 1:
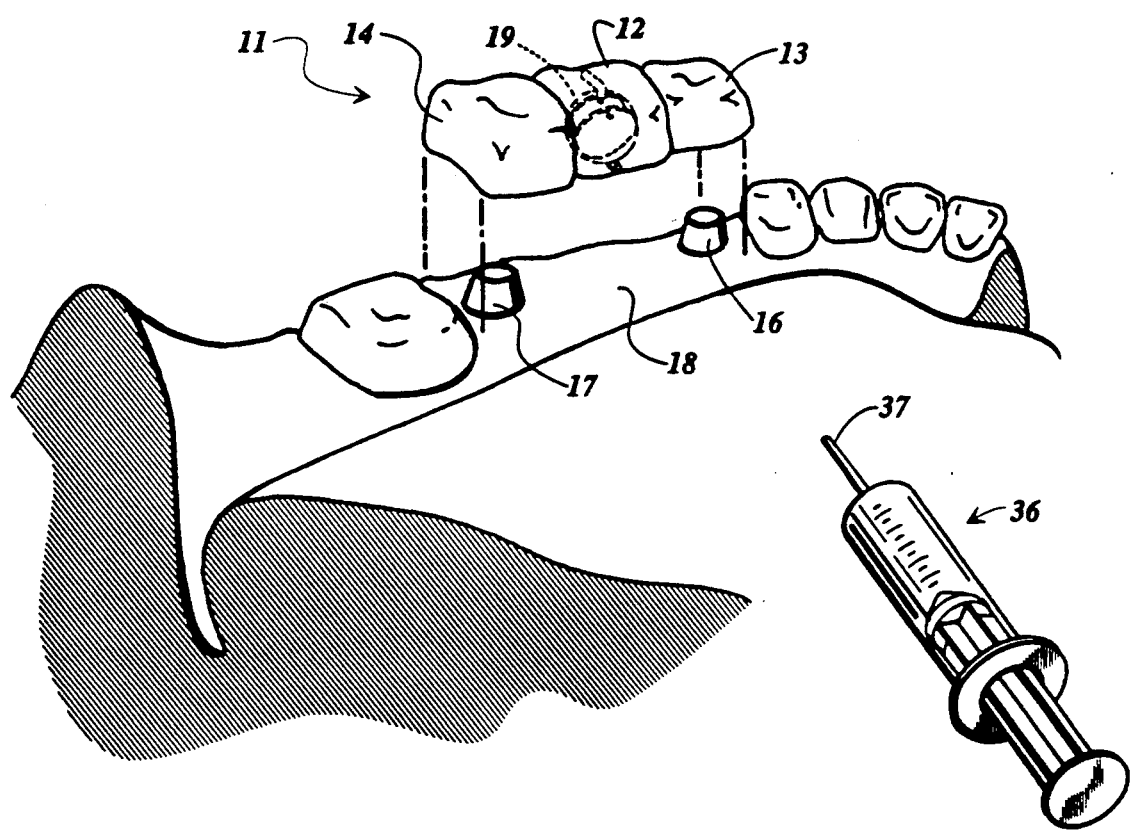
FIG. 1 is a partial perspective view showing placement in the mouth of a dental bridge that embodies principles of the invention in a preferred form.

Referring now in more detail to the drawings, in which like numerals refer to like parts throughout the several views, FIG. 1 illustrates a dental bridge 11 that embodies principles of the present invention in a preferred form. The bridge 11 is seen to comprise a central artificial tooth 12 that is formed with and wedged between a front artificial tooth 13 and a rear artificial tooth 14. Such bridges are commonly used to span gaps left by a missing tooth and are usually fabricated from porcelein using modeling techniques well known to dental technicians. The bridge 11 is seen to be mountable and securable in a wearer's mouth on a pair of spaced stubs 16 and 17 that previously have been prepared by grinding down one of the patient's natural teeth on either side of a gap 18 to be spanned by the bridge. Such grinding is, or course, performed by a dentist or other qualified person.

Figure 2:
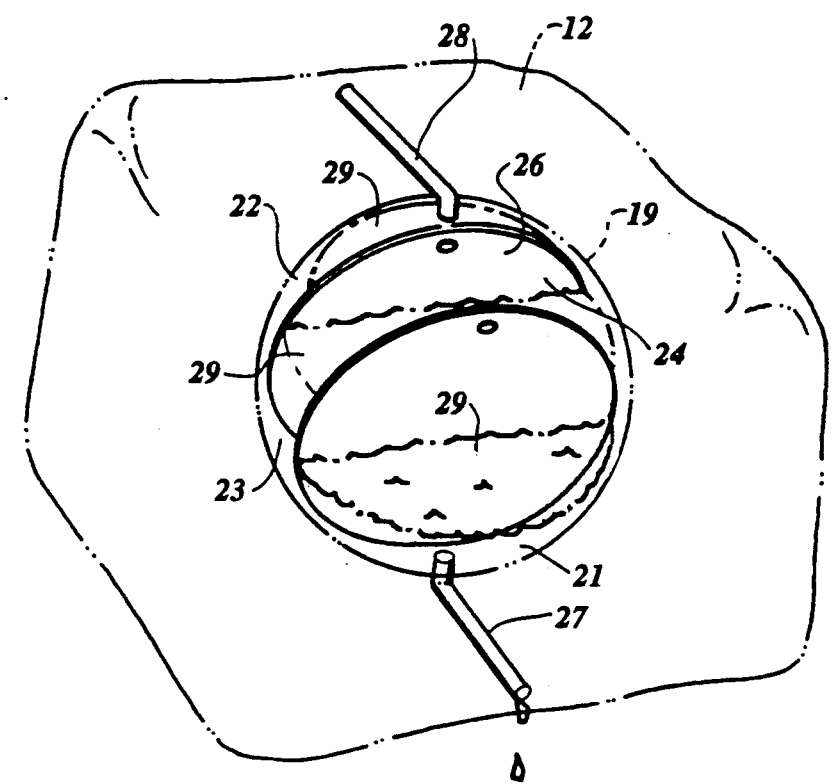
FIG. 2 is a perspective partially transparent view of the central artificial tooth of the bridge showing a preferred configuration and placement of the fluid bearing cavity therein.

As best seen in FIG. 2, the central artificial tooth 12 of bridge 11 is formed with a generally spherical interior cavity 19 that is separated by a pair of spaced walls 24 and 26 into an inner chamber 21, normally positioned adjacent the interior of the mouth, an outer chamber 22, normally positioned adjacent the cheek, and a central chamber 23 disposed between the inner and outer chambers.

A first duct or passageway 27 communicates between the lower portion of the cavity inner chamber 21 and the inner face of the tooth 12 for dispensing liquid from the inner chamber of the cavity into the mouth. A second passageway 28 communicates between the upper portion of the cavity outer chamber 22 and the outer face of the tooth 12 to provide venting of the cavity so that liquid can be displaced progressively with air as it is dispensed into the mouth. A liquid 29 such as, for example, medication or breath freshener, is seen partially filling each of the chambers 21, 22, and 23 of the cavity 19. It will be understood that in FIG. 2, the central artificial tooth 12 and consequently the cavity 19, walls 24, and passageways 27 and 28 are shown in the orientations that they normally assume with the wearer of the bridge standing or sitting in an upright position.

Figure 3:
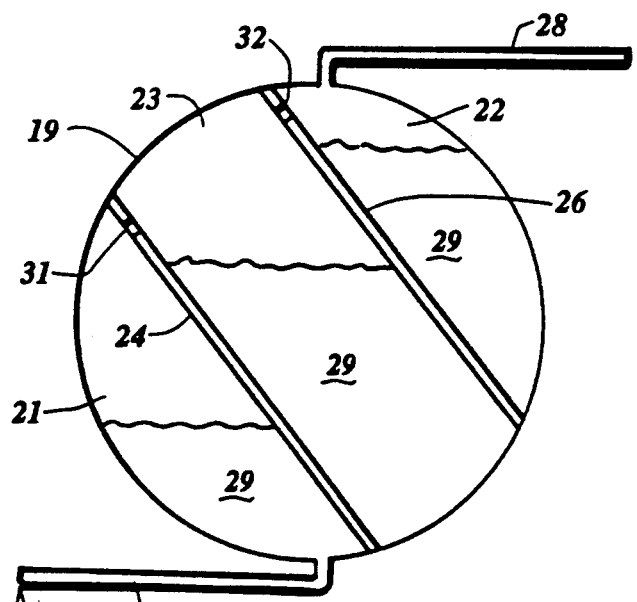
FIG. 3 is a side elevational view showing orientations of the elements of the cavity with a wearer in an upright position.

FIG. 3 is a side elevational view showing the cavity 19 and its associated elements as seen from the right side of the tooth 12 in FIG. 2 and as oriented with the bridge wearer standing or sitting in an upright position, i.e., the position normally assumed during daytime or waking hours. In this orientation, the walls 24 and 26, which separate the chambers of the cavity 19, are seen to be oriented or sloped upwardly from the exterior face of the tooth 12 toward the interior face thereof. While various degrees of slope might be employed, it has been found advantageous to position the walls to slope at an angle of approximately 45° with respect to the vertical when the bridge wearer assumes an upright or standing position.

The wall 24 is formed with a small hole or opening 31 in its upper peripheral portion that communicates between the central chamber 23 and the inner chamber 21 of the cavity 19. Similarly, wall 26 is formed with a hole or opening 32 in its upper peripheral portion with the hole 32 communicating between the outer chamber 22 of the cavity and the central chamber 23 thereof.

With the bridge wearer standing and the cavity elements oriented as shown in FIG'S. 2 and 3, fluid 29 is dispensed slowly from the inner chamber 21 through the first passageway 27 and into the mouth. The rate at which fluid is dispensed is dependent upon the diameter of the passageway 27 and upon the viscosity of the fluid being dispensed. In this regard, for use with fluid of a particular viscosity, the size of passageway 27 can be chosen such that the fluid is dispensed at the most desirable predetermined rate.

As can be seen in FIG. 3, fluid 29 is dispensed into the mouth as long as the wearer stands in an upright position or until the inner chamber 21 of the cavity 19 is depleted if such depletion occurs while the wearer is still standing. The inner chamber 21 can thus be sized to accommodate a predetermined prescribed dosage of fluid for dispensing progressively into the mouth during waking hours. In this regard, the placement of holes 31 and 32 in the upper peripheral edge portions of walls 24 and 26 respectively insures that only the measured dosage of liquid within the inner chamber 21 is dispensed during waking hours and that liquid within chambers 22 and 23 is reserved for future use as described in more detail below.

Figure 4:
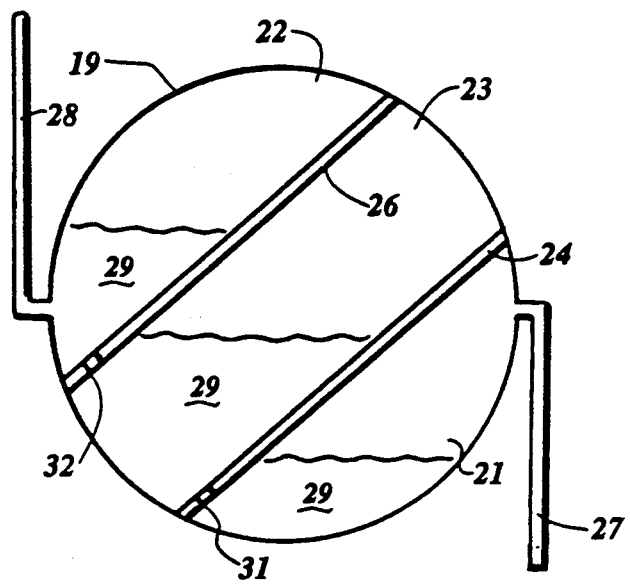
FIG. 4 is a side elevational view illustrating orientations of cavity elements with a wearer lying in a reclined position on one side.
Figure 5:
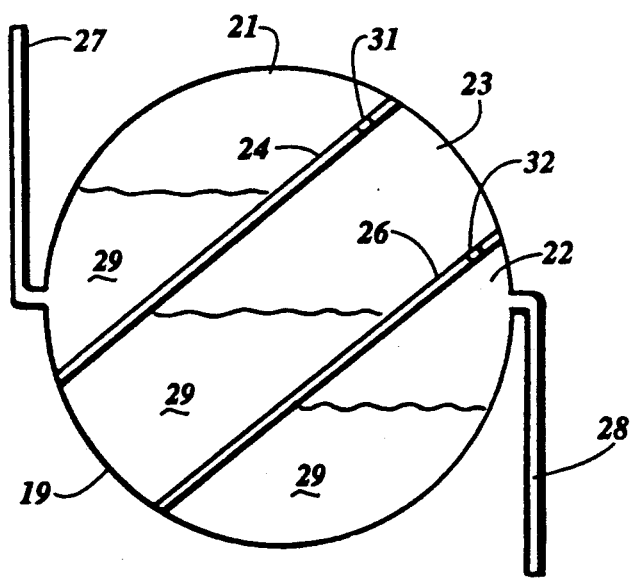
FIG. 5 is a side elevational view illustrating orientation of cavity elements as they appear with a wearer lying in a reclined position on his opposite side.

FIG'S. 4 and 5 respectively illustrate the orientations of the cavity 19, its interior walls 24 and 26, and passageways 27 and 28 when a wearer of the bridge 11 is lying in a reclined position on alternate sides of his or her body. These are the two positions most commonly assumed by individuals at night during sleep or rest. More specifically, with a dental bridge embodying this invention mounted in the lower left jaw of a wearer as shown in FIG. 1, FIG. 4 illustrates the orientation of cavity elements as they appear with the wearer lying on his right side while FIG. 5 illustrates the orientation of these elements with the wearer lying on his left side. It will be understood, however, that this selected placement of the bridge and thus the correlation between FIG'S. 4 and 5 and the lying positions of a wearer are exemplary only. The principals discussed hereinbelow are, however, equally applicable to alternate placements of the bridge and their corresponding correlations.

With reference to FIG. 4, as the wearer lies in a reclined position on his right side, the fluid 29 within outer chamber 22 and the central chamber 23 flows through openings 31 and 32 to refill the inner chamber 21. The placement and orientation of the passageways 27 and 28 when the wearer is in this position insures that fluid 29 does not escape into the wearer's mouth through either of the passageways. Thus, fluid dispensing is automatically discontinued when the wearer reclines for sleep or rest.

FIG. 5 illustrates the orientation of the cavity and its associated elements when a wearer of the bridge 12 lies on his left side. Here, again, the placement and orientation of passageways 27 and 28 insures against dispensing of fluid into the patient's mouth, thereby discontinuing the dispensing process automatically. Furthermore, with the wearer in this position, unwanted flow of fluid 29 from the inner chamber 21 back into the central and outer chambers 23 and 22 respectively is prevented because the openings 31 and 32 lie above the fluid levels in the respective chambers. It can thus be seen that a one-way flow is developed from the outer and central chambers 22 and 23 respectively into the inner chamber 21 thereby refilling the inner chamber for dispensing fluid when the patient again rises to an upright position.

In this regard, the rate at which the inner chamber 21 is refilled during sleeping hours is proportional to the size of openings 31 and 32, the viscosity of the fluid 29, and the proportion of the wearers sleeping time spent on his or her right side (or on the side that orients the chamber as shown in FIG. 4 for alternate placements of the bridge). Assuming that the wearer spends approximately one-half of his time on his right side, openings 31 and 32 can be sized according to fluid viscosity to fill the innermost chamber 21 with a predetermined volume of fluid 29 during sleep. Such could be important when dispensing medicines with critical dosage requirements. Alternatively, opening 31 and 32 could be formed with a relatively large size to insure that the inner chamber 21 is completely filled each night for dispensing fluid continuously throughout the following day. This alternative might be important when dispensing non-dosage critical fluids such as breath freshening solutions.

The cavity 19 and its associated walls 24 and 26 and passageways 27 and 28 can be formed within an artificial tooth or other dental prostheses using a number of well known fabrication methods commonly employed by dental technicians. Such techniques might include traditional wax-cast investment processes or, alternatively, the cavity 19 could be formed separately of a suitable material such as silver and imbedded within the tooth during casting and curing thereof. Such techniques are not discussed in detail here since they are generally well understood by dental technicians of ordinary skill in this art.

In use, a wearer of a bridge or other dental prostheses that embodies the present invention periodically fills the chambers of the cavity with fluid to be dispensed. Such filling is preferably accomplished by means of a common syringe 36 (FIG. 1) having a tip 37 that can be inserted into or abutted against the end of one of the passageways 27 and 28. The fluid 29 is then simply injected into the cavity 19 by appropriate manipulation of the syringe plunger.

With the cavity 19 thus filled, the fluid is dispensed progressively and automatically into the mouth during daytime or waking hours as described in detail hereinabove. During night time or sleeping hours, no or very little fluid is dispensed and the inner chamber 21 is refilled automatically from the outer and central chambers 22 and 23 respectively as illustrated in FIG. 4. Upon arising the following day, fluid from the refilled inner chamber 22 is again dispensed automatically and progressively throughout the day into the mouth. When the fluid supply within the cavity 19 is depleted, the wearer need only refill the cavity with the syringe for continued use.

The invention has been described above in terms of specific preferred embodiments. It will be obvious to those of skill in the art, however, that many changes might be made to the illustrated embodiments within the scope of this invention. For example, the invention has been illustrated as being embodied in a dental bridge. Obviously, the invention could also be embodied in many types of dental prostheses, such as dentures or crowns, or in separate devices for mounting in the mouth. Also, the chamber 19 has been illustrated as spherical in shape with three interior chambers. Other shapes and numbers of chambers might also be employed to meet specific needs or purposes as desired. These and many other modifications, deletions, and additions might be made to the embodiments illustrated herein above without departing from the spirit and scope of the invention as set forth in the claims.

We claim:

1. An apparatus for progressively dispensing a liquid substance into a wearer's mouth with said apparatus comprising:
    a vessel in the form of a dental prosthesis adapted to be mounted within the wearer's mouth;
    said vessel having an interior cavity adapted to contain the liquid substance to be dispensed;
    a first wall disposed in said cavity with said first wall being sized and positioned to define within said cavity a first chamber and a second chamber;
    said first wall being formed with an opening extending therethrough and communicating between said first and said second chamber;
    a first passageway adapted to communicate between said first chamber and the interior of a wearer's mouth when said vessel is mounted within the mouth, said first passageway being positioned and configured to deliver liquid from said first chamber into the mouth when the wearer is in an upright position; and
    a second passageway adapted to communicate between said second chamber and the interior of a wearer's mouth when said vessel is mounted within the mouth, said second passageway being positioned and configured to permit ingress of air into said second chamber as liquid is dispensed from said first chamber.

2. The apparatus of claim 1 and wherein said dental prothesis comprises a dental bridge.

3. The apparatus of claim 1 and wherein said vessel when mounted has an inner face positioned adjacent the interior portion of the mouth and an outer face positioned adjacent the cheek and wherein said first chamber is defined adjacent said inner face of said vessel and said second chamber is defined adjacent said outer face of said vessel, said first passageway being positioned and configured to communicate through said inner face of said vessel.

4. The apparatus of claim 3 and wherein said first wall is positioned to slope upwardly from a position adjacent the outer face of said vessel toward a position adjacent the inner face of said vessel when the wearer is in an upright orientation.

5. The apparatus of claim 4 and wherein said opening is positioned in the upper peripheral portion of said first wall when the wearer is in an upright orientation.

6. The apparatus of claim 5 and wherein said first passageway communicates with said first chamber at the lower portion of said cavity when the wearer is in an upright orientation.

7. The apparatus of claim 6 and wherein said second passageway communicates with said second chamber at the upper portion of said cavity when the wearer is in an upright orientation.

8. The apparatus of claim 7 and further comprising a second wall disposed within said cavity spaced from said first wall and defining within said cavity a third chamber positioned between said first chamber and said second chamber, said second wall being formed with an opening extending therethrough and communicating between said third chamber and its adjacent chamber.

9. A dental prosthesis adapted to dispense fluid automatically and progressively into a wearer's mouth, said dental prosthesis comprising:
   a body simulating at least one tooth with said body having an upper portion and a lower portion when the wearer is in an upright orientation;
   said body being formed with an interior cavity adapted to receive and contain fluid to be dispensed;
   first and second walls positioned and oriented within said cavity to define therein a first chamber located nearest the interior of the wearer's mouth, a second chamber located nearest the wearer's cheek, and a third chamber positioned between said first and second chambers;
   each of said first and second walls being formed with an opening extending therethrough and communicating between adjacent chambers of said cavity;
   a first passageway formed in said body and communicating between said first chamber at the lower portion of said cavity and the interior of the wearer's mouth; and
   a second passageway formed in said body and communicating between said second chamber at the upper portion of said cavity and the interior of the wearer's mouth,
   whereby the cavity can be filled with fluid to be dispensed whereupon fluid in the first chamber is delivered progressively into the mouth through the first passageway with the second passageway providing a vent for ingress of air to displace dispensed fluid.

10. The dental prosthesis of claim 9 and wherein said first and second walls are substantially parallel and sloped within said cavity such that said first chamber is defined generally in the lower portion of said body and said second chamber is defined generally in the upper portion of said body and wherein each of said openings is formed in the upper peripheral portion of its respective wall whereby fluid is dispensed from the first chamber when the wearer is in an upright position and when the wearer reclines for sleep or rest, fluid dispensing is discontinued and the first chamber is refilled through the openings.

11. A breath freshening dental bridge comprising a body formed to simulate natural teeth with said body having an interior cavity adapted to receive and contain breath freshening fluid and a passageway communicating between said interior cavity and the interior of a wearer's mouth, said passageway being positioned and configured to deliver breath freshening fluid from said interior cavity progressively into a wearer's mouth when the wearer in an upright position and to prevent delivery of breath freshening fluid to the wearer's mouth when the wearer is in a reclined position.

12. The breath freshening dental bridge of claim 11 and wherein said cavity is chambered and wherein said passageway communicates with a selected chamber of said cavity.

* * * * *